(12) United States Patent
Minato

(10) Patent No.: US 6,419,668 B2
(45) Date of Patent: *Jul. 16, 2002

(54) SURFACE FASTENER AND PAPER DIAPER USING THE SURFACE FASTENER

(75) Inventor: Hitomi Minato, Macon, GA (US)

(73) Assignee: YKK Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/300,640

(22) Filed: Apr. 27, 1999

Related U.S. Application Data

(63) Continuation-in-part of application No. 08/938,956, filed on Sep. 26, 1997, now abandoned.

(30) Foreign Application Priority Data

Sep. 30, 1996 (JP) ................................................ 8-259257

(51) Int. Cl.⁷ .............................. A61F 13/15; A44B 1/04
(52) U.S. Cl. ........................ 604/391; 24/306; 24/304; 24/442
(58) Field of Search ........................ 24/306, 304, 442; 604/391

(56) References Cited

U.S. PATENT DOCUMENTS

| | | |
|---|---|---|
| 3,353,663 A | 11/1967 | Kayser et al. ............... 206/346 |
| 3,370,818 A | 2/1968 | Perr |
| 3,620,217 A | 11/1971 | Gellert |
| 4,043,340 A | 8/1977 | Cepuritis |
| 4,186,744 A | 2/1980 | Ness |
| 4,299,223 A * | 11/1981 | Cronkite ..................... 128/287 |
| 4,322,875 A | 4/1982 | Brown et al. |
| 4,523,333 A | 6/1985 | Spangler ....................... 2/49.3 |
| 4,699,622 A | 10/1987 | Toussant et al. |
| 4,706,914 A | 11/1987 | Ground |
| 4,869,724 A | 9/1989 | Scripps ....................... 604/389 |
| 5,176,670 A | 1/1993 | Roessler et al. |
| 5,176,671 A | 1/1993 | Roessler et al. |
| 5,462,540 A | 10/1995 | Caldwell |
| 5,586,595 A | 12/1996 | Takizawa et al. ........... 160/330 |
| 5,672,404 A | 9/1997 | Callahan, Jr. et al. |
| 6,115,891 A * | 9/2000 | Suenaga et al. ............... 24/442 |

FOREIGN PATENT DOCUMENTS

| | | | |
|---|---|---|---|
| CA | 2021538 | 7/1990 | .................... 13/15 |
| CA | 20241538 | 1/1992 | |
| DE | 4010567 | 10/1991 | |
| EP | 0693889 | 1/1996 | |
| FR | 2624353 | 6/1989 | |
| GB | 1181022 | 2/1970 | |
| JP | 1-29230 | 9/1989 | |
| JP | 2-5947 | 1/1990 | |
| WO | WO 95/03723 | 2/1995 | |

* cited by examiner

Primary Examiner—John G. Weiss
Assistant Examiner—Paul Shanoski
(74) Attorney, Agent, or Firm—Finnegan, Henderson, Farabow, Garrett, & Dunner, L.L.P.

(57) ABSTRACT

A surface fastener having a first substrate sheet having on its front surface hook-shaped engaging elements and on its rear surface a low-adhesion adhesive double coated tape to an outer surface of which a backing sheet is adhered, and a second substrate sheet having on its front surface loop-shaped engaging elements and on its rear surface an adhesive layer to an outer surface of which a peel paper is adhered. For attaching the surface fastener to a paper diaper, the adhesive layer of the second substrate sheet is adhered to a front covering portion of the diaper, while the adhesive double coated tape of the first substrate sheet is adhered to an attachment strip of a hip covering portion of the diaper after the backing sheet is peeled off. When casting off the diaper after using, the adhesive double coated tape is separated from the first substrate sheet so as to be left on the attachment strip and then the diaper is folded, whereupon the adhesive double coated tape on the attachment strip is adhered to an outer surface of the folded diaper to wrap up the diaper.

11 Claims, 7 Drawing Sheets

SURFACE FASTENER AND PAPER DIAPER USING THE SURFACE FASTENER

This is a continuation-in-part application of copending prior application Ser. No. 08/938,956, filed Sep. 26, 1997, now abandoned, which is incorporated herein by reference.

BACKGROUND OF THE INVENTION

1. Description of the Invention

This invention relates to a surface fastener to be used as a fastener of a disposable paper diaper, the surface fastener being improved in its attaching means so that the paper diaper is easy to handle.

2. Description of the Related Art

FIG. 10 of the accompanying drawings shows a paper diaper fastener which is disclosed in Japanese Utility Model Publication No. Hei 1-29230. In this known fastener, a plastic substrate tape 1' has on its one surface an adhesive layer 7' extending from the center to one end and a protective peel portion 8' extending from the center to the other end. On the other surface, the plastic substrate tape 1' has another protective peel portion 8' extending from the center to one end and another adhesive layer 7' extending from the center to the other end, which is a reverse arrangement to that on the one surface. The plastic substrate tape 1' is attached in a folded form to a paper diaper A' and, in use, the adhesive layer 7' is peeled off the protective peel portion 8' and is then adhered to a companion attaching section of the diaper A'.

Japanese Patent Laid-Open Publication No. Hei 2-5947 discloses a concept of using a surface fastener SF in a disposable diaper. As shown in FIG. 11, in the surface fastener, a thin strong flexible substrate plate 1 has on its front surface a multiplicity of resilient mushroom-shaped engaging elements 3" each having a stem 3"$b$ projecting upright from the front surface and a round head 3"$a$ at the top of the stem 3"$b$. This surface fastener is fixed to an end of a flexible elongated rectangular polymer tab and is provided with a low-viscosity pressure-sensitive adhesive agent so that it is kept in a folded form; in use, the surface fastener is unfolded and is then fastened with a companion surface fastener.

According to the first-named conventional diaper fastener in a form of the plastic tape 1', since the diaper A' is fastened by the adhesive layer 7', it is impossible to fasten the diaper A' with adequate firmness. Further, the adhesive layer 7' of the plastic tape 1' tends to touch the infant's skin which is very delicate when the diaper A' is in use, so that the infant might suffer atopic dermatitis and other skin diseases.

According to the second-named conventional diaper fastener in a form of a surface fastener, since the engaging elements 3" of the surface fastener SF have a very special shape, it is inevitable to use a very complicated processing means in manufacturing the surface fastener SF, and there is a danger that the pressure-sensitive adhesive agent on the polymer tab might touch the infant's skin and cause atopic dermatitis or other skin diseases when the diaper is in use.

SUMMARY OF THE INVENTION

A first object of this invention is to provide a surface fastener which is suitable for a disposable paper diaper and in which either an adhesive layer or an adhesive double coated tape has such a form as not to contact an infant's skin directly and which is easy to handle when the used paper diaper is to be cast off, at which time the used diaper is folded into a compact size and is wrapped in a simple manner.

A second object of the invention is to provide a surface fastener which is very simple to attach and handle with respect to a paper diaper.

A third object of the invention is to provide a surface fastener which is shaped into a form suitable for use in a paper diaper in view of relation between the adhesive strength of an adhesive layer and an adhesive double coated tape with respect to the surface fastener and the shape of engaging elements.

A fourth object of the invention is to provide a surface fastener which has a shape suitable for use in a paper diaper by specifying the surface fastener manufacturing means and shape.

A fifth object of the invention is to provide a surface fastener of which hook-shaped engaging elements are suitable for a paper diaper by specifying the hook-shaped engaging element manufacturing means.

A sixth object of the invention is to provide a paper diaper to which a surface fastener is attached in an optimal form and in which the surface fastener has such a shape that an adhesive layer and an adhesive double coated tape will not come into direct contact with an infant's skin.

A seventh object of the invention is to provide a paper diaper in which a surface fastener can be attached in a simple manner and which can be handled simply when it is to be cast off after using.

According to a first aspect of the invention, there is provided a surface fastener comprising: a first substrate sheet having on its front surface a multiplicity of first engaging elements and on its rear surface a first adhesive layer; a second substrate sheet having on its front surface a multiplicity of second engaging elements engageable with the first engaging elements and on its rear surface a second adhesive layer; the first adhesive layer having an adhesive strength smaller than that of said second adhesive layer.

Preferably, the first adhesive layer is an adhesive double coated tape and has on its outer surface a backing sheet adhered thereto, while the second adhesive layer has on its outer surface a peel paper adhered thereto.

According to a second aspect of the invention, the backing sheet has on its outer surface another adhesive layer to an outer surface of which another peel paper is adhered.

According to a third aspect of the invention, the second engaging elements of the second substrate sheet on which the first-mentioned adhesive layer is disposed are loop-shaped engaging elements, and the first engaging elements of the first substrate sheet on which the adhesive double coated tape is disposed are hook-shaped engaging elements.

According to a fourth aspect of the invention, at least one of the first and second substrate sheets is knitted or woven, and the engaging elements of one of the first and second substrate sheets are hook-shaped engaging elements and/or loop-shaped engaging elements.

According to a fifth aspect of the invention, hook-shaped engaging elements are molded on the front surface of the first substrate sheet by injection molding.

According to a sixth aspect of the invention, there is provided a paper diaper using a plurality of surface fasteners, comprising a front covering portion and a hip covering portion having a plurality of attachment strips at its opposite sides, each surface fastener comprising: a first substrate sheet having on its front surface a multiplicity of first engaging elements; a second substrate sheet having on its front surface a multiplicity of second engaging elements engageable with the first engaging elements and on its rear surface an adhesive layer adhered to each of the opposite sides of the front covering portion; and an adhesive double coated tape adhered to a rear surface of the first substrate sheet with an adhesive strength smaller than that of the adhesive layer, the adhesive double coated tape being adhered to each of the attachment strips of the hip covering portion.

According to a seventh aspect of the invention, a backing sheet is adhered to an outer surface of the adhesive double coated tape and has on a surface opposite to the tape an additional adhesive layer of which outer surface is adhered to each of the attachment strips of the hip covering portion.

According to an eighth aspect of the invention, the second engaging elements of each second substrate sheet on which the first-mentioned adhesive layer is disposed are loop-shaped engaging elements, and the first engaging elements of each first substrate sheet on which the adhesive double coated tape is disposed are hook-shaped engaging elements.

According to a ninth aspect of the invention, the first or second substrate sheet is knitted or woven, and the engaging elements of the first or second substrate sheets are hook-shaped engaging elements and/or loop-shaped engaging elements.

According to a tenth aspect of the invention, the hook-shaped engaging elements are molded on the front surface of the first substrate sheet by injection molding.

DETAILED DESCRIPTION OF THE PREFERRED EMBODIMENTS

Surface fasteners according to preferred embodiments and paper diapers using the surface fasteners will now be described in detail with reference to the accompanying drawings.

Recently application of surface fasteners, instead of adhesive tapes, to paper diapers has been on the increase. One of the reasons is that many infants having delicate skins suffer atopic dermatitis when they touch the adhesive tapes.

Figure 1:
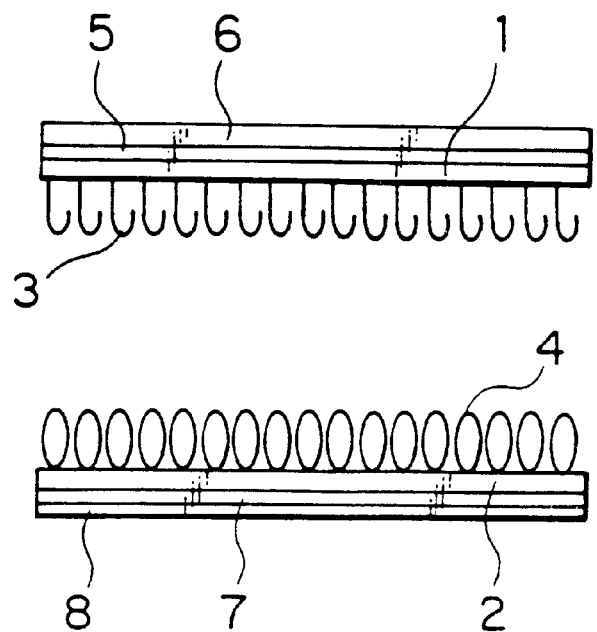
FIG. 1 is a front view of a surface fastener according to a first embodiment of this invention.

FIG. 1 shows a surface fastener according to a first embodiment of this invention which is designed in such a manner that an adhesive layer and an adhesive double coated tape would not touch the infant's skin when the surface fastener is used for a paper diaper. In the surface fastener, a male surface fastener member includes a first substrate sheet 1 having on its front surface a multiplicity of hook-shaped engaging elements 3, an adhesive double coated tape 5 adhered to a rear surface of the first substrate sheet 1, and a backing sheet 6 adhered to an outer surface of the tape 5. A female surface fastener member includes a second substrate sheet 2 having on its front surface a multiplicity of loop-shaped engaging elements 4, an adhesive layer 7 on a rear surface of the second substrate sheet 2, and a peel paper 8 adhered to an outer surface of the adhesive layer 7.

Figure 2:
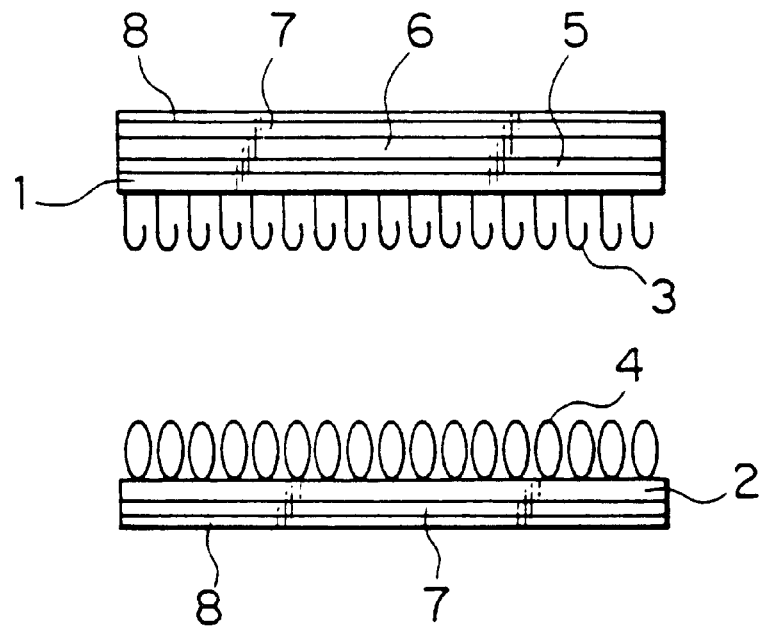
FIG. 2 is a front view of a modified surface fastener according to a second embodiment of the invention.

FIG. 2 shows an alternative surface fastener according to a second embodiment of the invention. In the modified surface fastener, a male surface fastener member includes a first substrate sheet 1 having on its front surface a multiplicity of hook-shaped engaging elements 3, an adhesive double coated tape 5 on a rear surface of the substrate sheet 1, a backing sheet 6 adhered to an outer surface of the adhesive double coated tape 5, an adhesive layer 7 on an outer surface of the backing sheet 6, and a peel taper 8 adhered to an outer surface of the adhesive layer 7. In the meantime, a female surface fastener member includes a second substrate sheet 2 having on its front surface a multiplicity of loop-shaped engaging elements 4, an adhesive layer 7 on a rear surface of the substrate sheet 2, a peel paper 8 adhered to an outer surface of the adhesive layer 7.

In the foregoing surface fasteners, the first and second substrate sheets 1, 2 are woven or knitted of synthetic fibers such as polyamide or polyester and, at the same time, the hook-shaped engaging elements 3 are formed from monofilament while the loop-shaped engaging elements 4 are formed from multifilament. The backing sheet 6 is made of thermoplastic resin. The adhesive double coated tape 5 and the adhesive layer 7 are made of rubber resin, acrylic resin, etc. The adhesive double coated tape 5 has an adhesive strength smaller than that of the adhesive layer 7.

Figure 3:
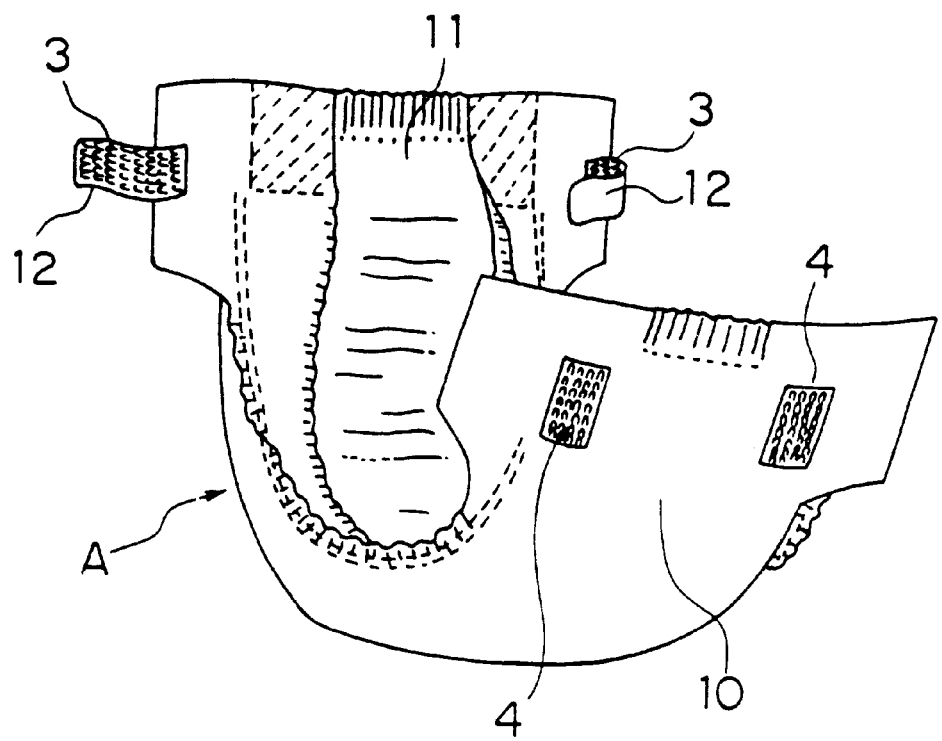
FIG. 3 is a perspective view showing a paper diaper in an opened posture.
Figure 4:
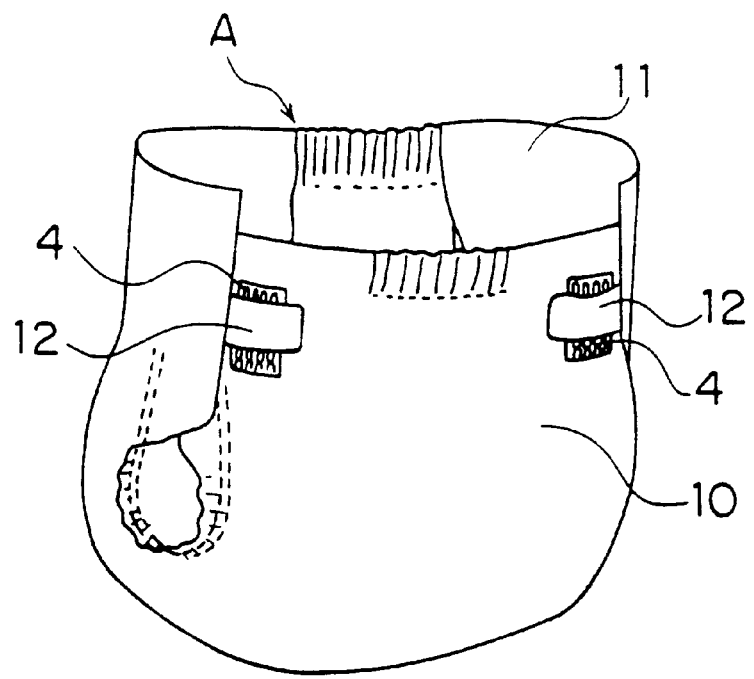
FIG. 4 is a perspective view showing the paper diaper in a fastened posture.

FIGS. 3 and 4 respectively shows an example in which the foregoing surface fasteners are used in a paper diaper A. A pair of female surface fastener members are attached to the outer surface of a front covering portion 10 of the paper diaper A at its opposite sides, while a pair of male surface fastener members are attached to inner surfaces of a pair of attachment strips 12 fixed to opposite sides of a hip covering portion 11 of the paper diaper A.

Figure 5:
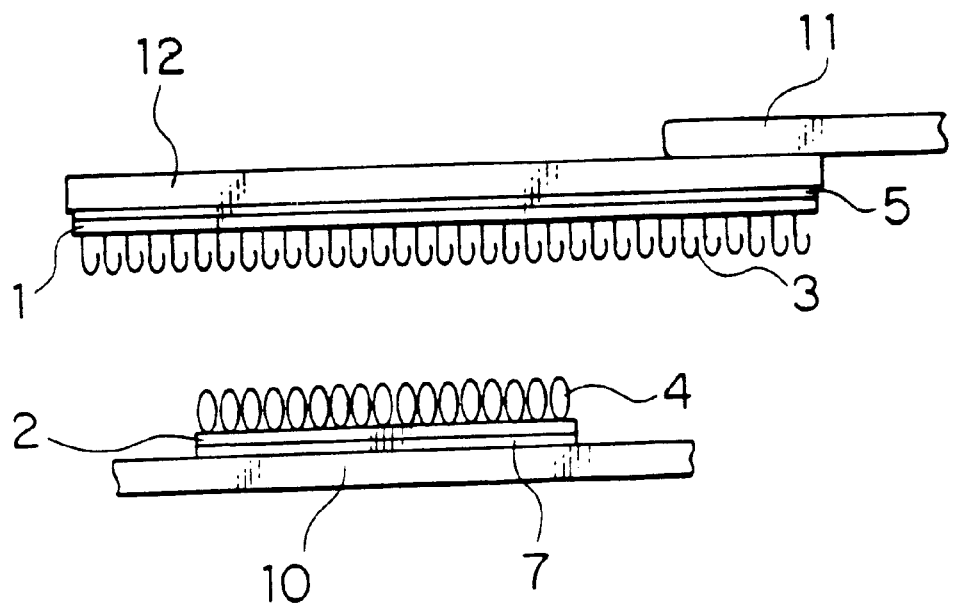
FIG. 5 is a side view showing one example of use of the surface fastener of FIG. 1.

FIG. 5 shows one example in which the surface fastener of FIG. 1 is used in a paper diaper A. In this example, the second substrate sheet 2 of each female surface fastener is attached to each of opposite sides of the front covering portion 10 of the paper diaper A as shown in FIG. 5 by the adhesive layer 7 with the peel paper 8 peeled off the rear surface thereof. In the meantime, the first substrate sheet 1 of each male surface fastener of FIG. 1 is adhered to each of the attachment strips 12 of the hip covering portion 11 of the paper diaper A by the adhesive double coated tape 5 with the backing sheet 6 peeled off the rear surface thereof. In using the diaper A, the hook-shaped engaging elements 3 of the first substrate sheet 1 are brought into engagement with the loop-shaped engaging elements 4 of the second substrate sheet 2 as the female surface fastener is pressed against the corresponding male surface fastener. In an alternative form, a pair of backing sheets 6 may be attached directly to the hip covering portion 11 for substitution for the attachment strips 12.

For casting off the paper diaper A after using, with the hook-shaped engaging elements 3 kept in engagement with the loop-shaped engaging elements 4, each attachment strip 12 is pulled outwardly so as that the adhesive double coated tape 5 is peeled off the first substrate sheet 1 and hence stay on the attachment strip 12, and then the paper diaper A is folded, whereupon the paper diaper A is wrapped in a compact size by adhering the adhesive double coated tapes 5 of the attachment strips 12 to the outer surface of the folded paper diaper A at some positions thereof.

Figure 6:
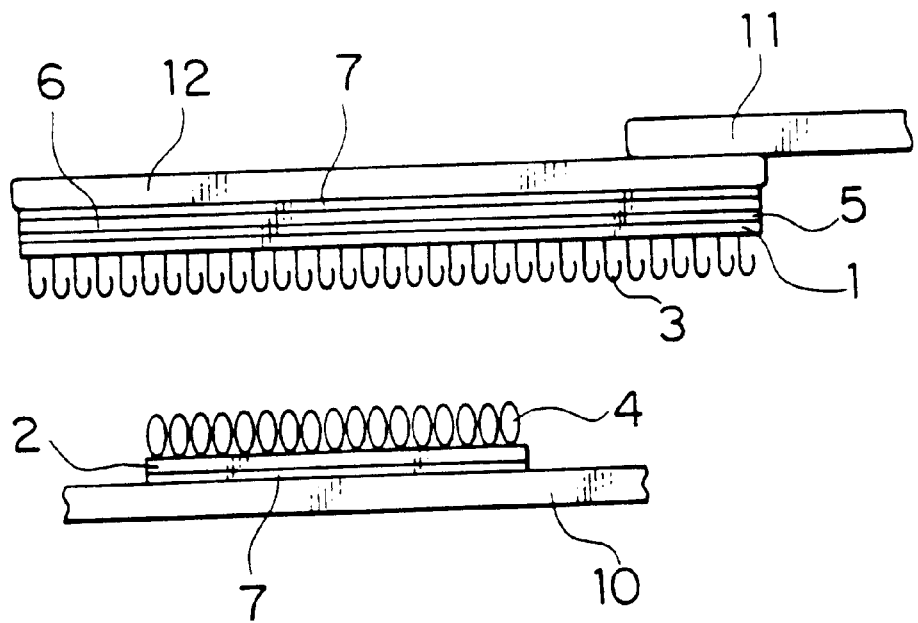
FIG. 6 is a side view showing one example of use of the surface fastener of FIG. 2.
Figure 7:
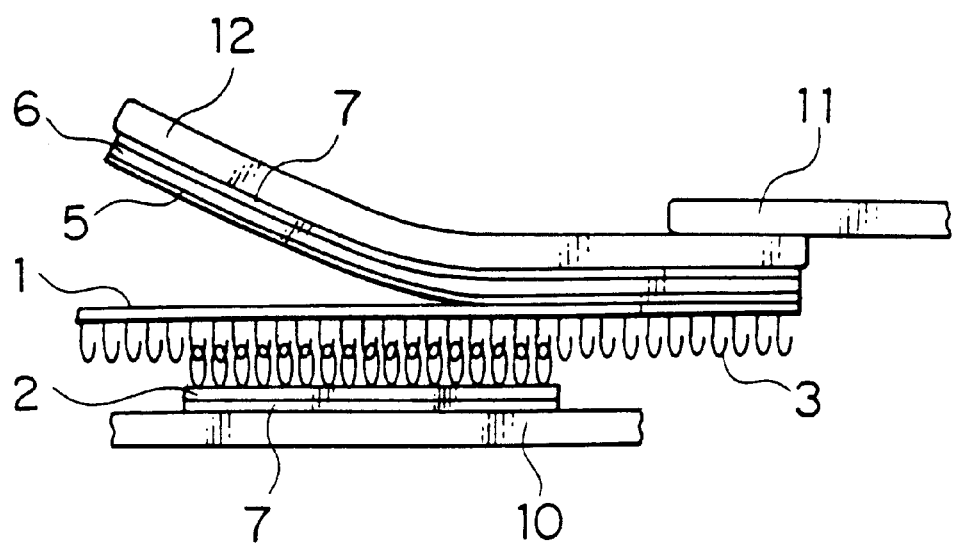
FIG. 7 is a side view showing the manner in which the surface fastener of FIG. 6 is separated.

FIGS. 6 and 7 respectively shows another example in which the surface fastener of FIG. 2 is used in a paper diaper A. In this example, the second substrate sheet 2 of each female surface fastener member is attached to each of opposite sides of the front covering portion 10 of the paper diaper A by the adhesive layer 7 with the peel paper 8 peeled off. In the meantime, the first substrate sheet 1 of each male surface fastener member is attached to each of the attachment strips 12 of the hip covering portion 11 of the paper diaper A by the adhesive layer 7 with the peel paper 8 peeled off.

For casting off the paper diaper A after using, one end of the attachment strip 12 is pulled outwardly to separate the adhesive double coated tape 5 from the first substrate sheet 1 so as to stay on the backing sheet 6. After it is folded, the paper diaper A is wrapped by adhering the separated attachment strips 12 to the outer surface of the folded paper diaper A at some positions.

Figure 8:
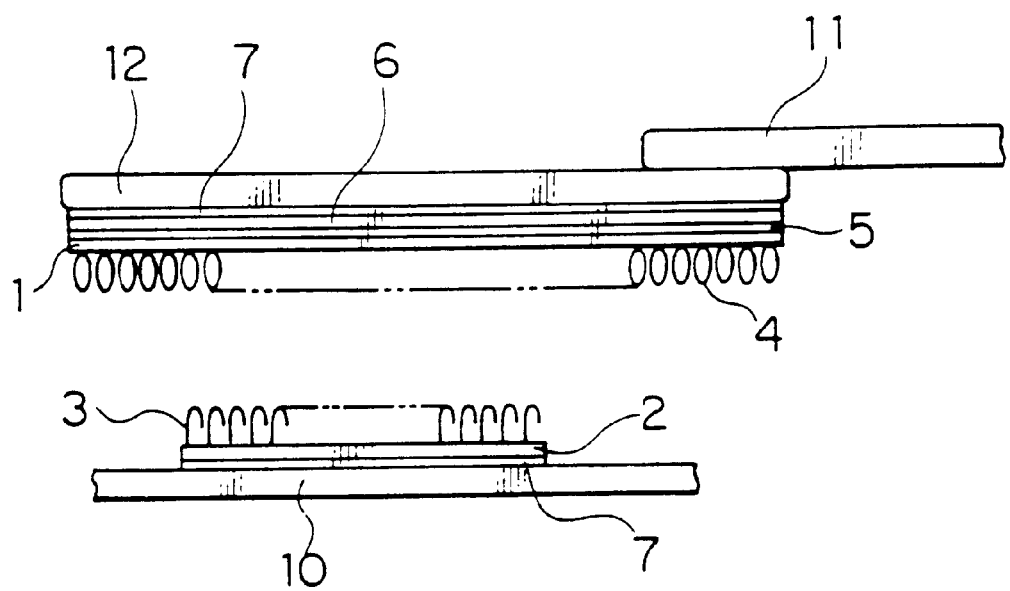
FIG. 8 is a side view showing one example of use of another modified surface fastener according to a third embodiment of the invention.

FIG. 8 shows a third embodiment in which a modified surface fastener is used in a paper diaper A. In this modified surface fastener, the male surface fastener member includes a second substrate sheet 2 having on its front surface a multiplicity of hook-shaped engaging elements 3, an adhesive layer 7 on a rear surface of the second substrate sheet 2, and a peel paper 8 adhered to an outer surface of the adhesive layer 7, while the female surface fastener member includes a first substrate sheet 1 having on its front surface a multiplicity of loop-shaped engaging elements 4, an adhesive double coated tape 5 adhered to a rear surface of the substrate sheet 1, a backing sheet 6 adhered to an outer surface of the adhesive double coated tape 5, and another adhesive layer 7 and a peel paper 8 on an outer surface of the backing sheet 6. The male surface fastener member is attached to each of opposite sides of the front covering portion 10 of the paper diaper A by the adhesive layer 7 with the peel paper 8 peeled off the adhesive layer 7. In the meantime, the female surface fastener member is attached to each of the attachment strips 12 of the hip covering portion 11 of the paper diaper A by its adhesive layer 7 with the peel paper 8 peeled off.

Figure 9:
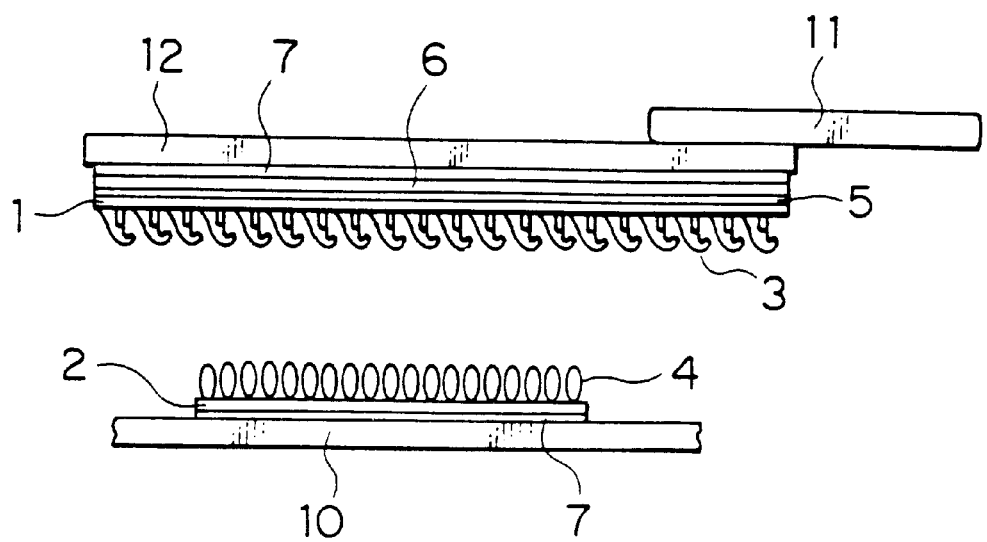
FIG. 9 is a side view showing one example of use of an injection-molded surface fastener according to a fourth embodiment.
Figure 10:
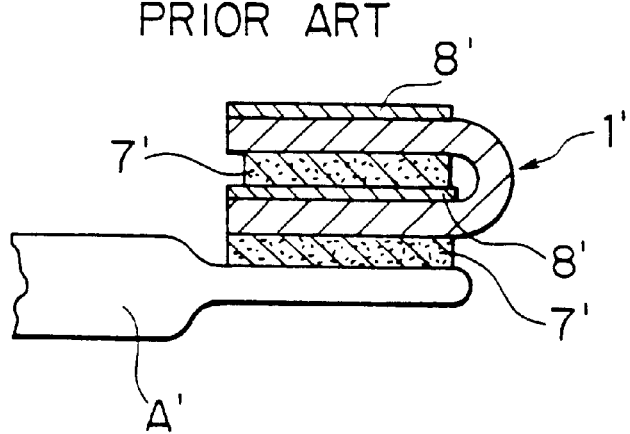
FIG. 10 is a fragmentary cross-sectional view of a conventional surface fastener used in a paper diaper.
Figure 11:
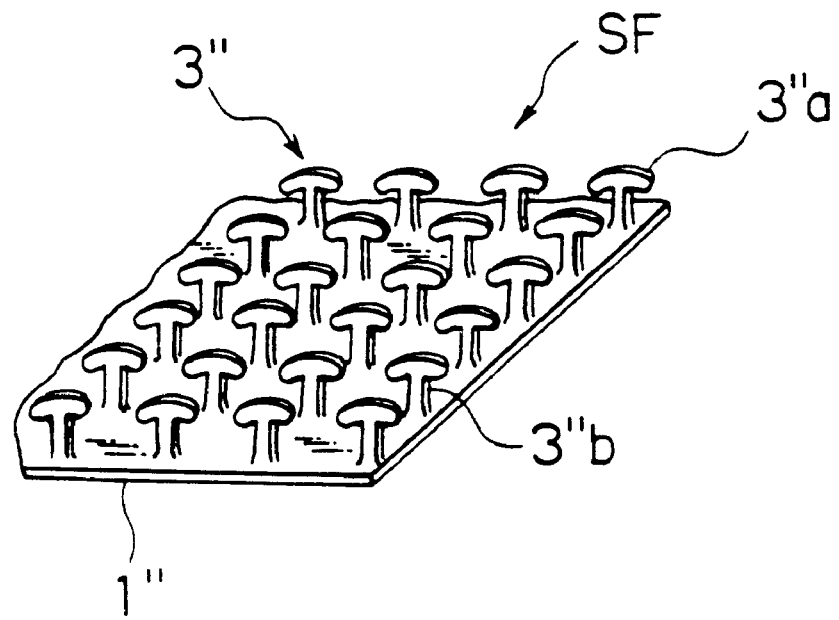
FIG. 11 is a fragmentary perspective view of another conventional surface fastener used in a paper diaper.

FIG. 9 shows a fourth embodiment in which another modified surface fastener is used in a paper diaper A. In this modified surface fastener, the female surface fastener member is identical with that of the previous embodiment, while the male surface fastener member is different from that of the previous embodiment in that the first substrate sheet 1 and the hook-shaped engaging elements 3 are integrally molded by injection molding using thermoplastic resin. For attaching the modified surface fastener to the paper diaper A, likewise in the previous example, the second substrate sheet 2 of each female surface fastener is attached to each of opposite sides of the front covering portion 10 of the paper diaper A by the adhesive layer 7 which is disposed on the rear surface of the second substrate sheet 2.

The molded male surface fastener member has on the rear surface of the first substrate sheet 1 an adhesive double coated tape 5, a backing sheet 6 adhered to an outer surface of the adhesive tape 5, an adhesive layer 7 and a peel paper 8 on an outer surface of the backing sheet 6. In use, with the peel paper 8 peeled off, the male surface fastener member is attached to each attachment strip 12 of the hip covering portion 11 of the paper diaper A by the adhesive layer 7. The used paper diaper A is cast off in the same manner as the previous example.

In manufacturing a surface fastener by weaving or knitting, a surface fastener may be woven or knitted in such a manner that hook-shaped engaging elements 3 and loop-shaped engaging elements 4 are arranged in combination on the front surface of each of the first and second substrate sheets 1, 2. The resulting surface fastener member can be attached to either of a male or female surface fastener on the paper diaper A.

Figure 12:
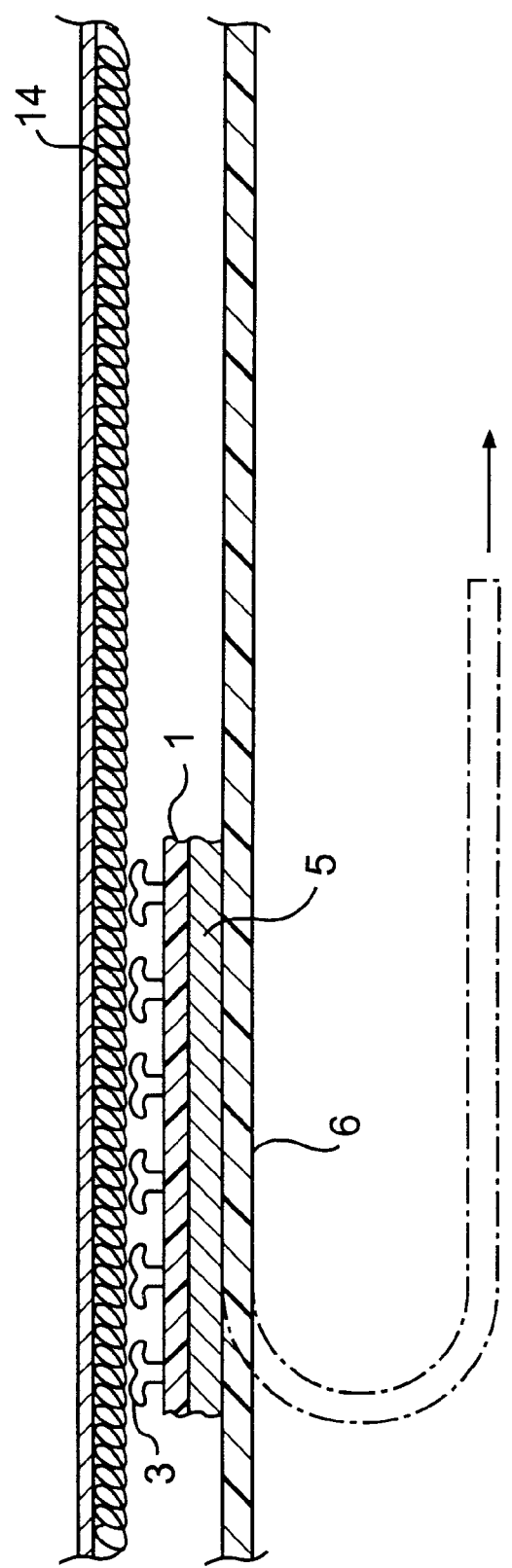
FIG. 12 is a side view showing an example of a surface fastener according to the principles of the present invention.

Another example of a surface fastener according to the present invention is shown in FIG. 12 as a side view. The surface fastener has a female surface fastener member including a knitted fabric 14 and a male surface fastener member which is releasably engageable with the female surface fastener member. The male surface fastener member has a plurality of hook-shaped engaging elements 3 on a substrate sheet 1. An adhesive layer 5 adheres the substrate sheet 1 to a backing sheet 6.

Examples of the components may include the following. The knitted fabric 14 can be a Brush-Nylon weighing 43 g/m$^2$ and manufactured by Sitip Company. The substrate sheet 1 and hook-shaped engaging elements 3 can be those described in U.S. Pat. No. 5,755,015. Durotac 134-4008 available from National Starch & Chemical, Japan, may be used for the adhesive layer 5. The Durotac 134-4008 adhesive has a chemical name of synthetic rubber hot melt adhesive and is a styrene-iso-prene-styrene block copolymer. The backing sheet 6 can be an oriented polypropylene film having a thickness of 20 $\mu$m.

One application of the surface fastener shown in FIG. 12 is for use on a diaper. An attachment strip of the diaper may be formed of a non-woven fabric covered with the backing sheet 6. Accordingly, the side of the backing sheet 6 opposite the adhesive layer 5 would cover the non-woven fabric of the diaper attachment strip.

The adhesive strength of the adhesive layer 5 is less than the engaging strength of the hook-shaped engaging elements 3 engaged with the knitted fabric 14. Accordingly, when the backing sheet 6 is peeled in a peeling direction as shown by the arrow in FIG. 12, the hook-shaped engaging elements 3 remain engaged with the knitted fabric 14 as the backing sheet 6 is peeled away from the substrate sheet 1. Depending on the adhesive strength between the adhesive layer 5 and the substrate sheet 1 and the adhesive strength between the adhesive layer 5 and the backing sheet 6, the adhesive layer 5 will remain either on the substrate sheet 1 or the backing sheet 6. For example, the adhesive layer 5 may remain with the film 6 when the film 6 is part of a diaper attachment strip so that the attachment strip and the adhesive layer 5 can be used to neatly wrap the diaper after use.

The peeling strength of a surface fastener of FIG. 12 made with the components mentioned above has been measured. The knitted fabric 14 is the Brush-Nylon, the substrate sheet 1 and the hook-shaped engaging elements 3 are those in U.S. Pat. No. 5,755,01 5, the adhesive layer 5 is the Durotac 134-4008, and the backing sheet 6 is the 20 $\mu$m thick oriented polypropylene film. Peeling strength was measured as a 180° peeling strength which means the backing sheet 6 was peeled in the direction of the arrow shown in FIG. 12. The 180° peeling strength was measured as a force in grams per centimeter of width of the surface fastener. The width of the surface fastener shown in FIG. 12 would be in the direction perpendicular to the page showing the side view of FIG. 12.

The 180° peeling strength between the knitted fabric 14 and the hookshaped engaging elements 3 was found to be 44.3 g/cm. The 180° peeling strength between the adhesive layer 5 and the oriented polypropylene film 6 (back sheet) was found to be 25 g/cm. The 180° peeling strength between the adhesive layer 5 and the film 6 was less than the 180° peeling strength between the knitted fabric 14 and the hook-shaped engaging elements 3. As such, the hook-shaped engaging elements 3 will remain engaging with the knitted fabric 14 when the backing sheet 6 is peeled from the surface fastener.

The female surface fastener member of the surface fastener in FIG. 12 is shown as a knitted fabric 14. However, the female surface fastener member can have other constructions, such as, the female surface fastener member shown in FIG. 1 having loop-shaped engaging elements 4 on a substrate sheet 2 and an adhesive layer 7 on a rear surface of the substrate sheet 2. Of course, the strength of the adhesive layer 7 would be greater than the strength of the adhesive double coated tape 5 so that the backing sheet 6 with the adhesive double coated tape 5 can be peeled from the surface fastener while the remaining components of the surface fastener remain connected together.

Referring to FIG. 1, the principles of the present invention discussed with reference to FIG. 12 would apply. For example, the adhesive strength of the adhesive double coated tape 5 at 25 g/cm would be less than the adhesive strength between the hook-shaped engaging elements 3 and the loop-shaped engaging elements 4 and also less than the adhesive strength of the adhesive layer 7. Accordingly, the adhesive layer 7 would have a peeling strength greater than 25 g/cm.

The foregoing surface fasteners and the foregoing paper diapers using the surface fasteners have the following advantageous results:

According to a first aspect of the invention, partly since the first substrate sheet 1 has on its front surface multiplicity of first engaging elements 3 or 4 and on its rear surface an adhesive double coated tape 5 to an outer surface of which a backing sheet 6 is adhered and partly since the second substrate sheet 2 has on its front surface a multiplicity of second engaging elements 3 or 4 and on its rear surface an adhesive layer 7 to an outer surface of which a peel paper 8 is adhered and partly since the adhesive strength of the adhesive double coated tape 5 is smaller than that of the adhesive layer 7, it is possible to separate a garment from the surface fastener with its male and female engaging elements 3, 4 kept in engagement with one another, thus it is possible to handle the surface fastener very simply especially when used in a disposable paper diaper.

According to a second aspect of the invention, since an adhesive layer 7 and a peel paper 8 are disposed on the backing sheet 6 on a side opposite to the adhesive double coated tape 5, it is possible to handle the surface fastener much more simply especially when used in a disposable paper diaper.

According to a third aspect of the invention, since the substrate sheet 2 of the female surface fastener member has an adhesive layer 7 while the substrate sheet 1 of the male surface fastener member has an adhesive double coated tape 5, it is possible to separate a garment at the adhesive double coated tape 5 on the male surface fastener member and to make the surface fastener optimal in view of attachment, strength and handling especially when used in a disposable paper diaper.

According to a fourth aspect of the invention, since one of the first and second substrate sheets 1, 2 is woven or knitted and has hook-shaped engaging elements 3 and/or loop-shaped engaging elements 4, it is possible to separate a garment from the surface fastener easily with male and female engaging elements 3, 4 kept in engagement with one another and to combine the surface fastener member with any kind of companion surface fastener member.

According to a fifth aspect of the invention, since the hook-shaped engaging elements 3 are molded on the substrate sheet 1 or 2 by injection molding, it is possible to separate a garment simply with male and female engaging elements 3, 4 kept in engagement with one another.

According to a sixth aspect of the invention, partly since the substrate sheet 1 or 2 of one surface fastener member is attached to the front covering portion 10 of the paper diaper A by an adhesive layer 7, and partly since the substrate sheet 1 or 2 of the other surface fastener member is attached to the attachment strip 12 of the hip covering portion 11 of the paper diaper A by an adhesive double coated tape 5, it is possible to separate a garment with male and female engaging elements 3, 4 kept in engagement with one another, thus preventing the adhesive layer 7 or the adhesive double coated tape 5 from directly touching the infant's skin so that the infant is kept free from skin diseases such as atopic dermatitis.

According to a seventh aspect of the invention, since a backing sheet 6 is adhered at one side surface to the adhesive double coated tape 5 and is adhered at the other side surface to the attachment strips 12 of the hip covering portion 11 by an adhesive layer 7, it is possible to handle the paper diaper very simply.

What is claimed is:

1. A surface fastener comprising:
    a first substrate sheet sheet having on a front surface a plurality of first engaging elements and on a rear surface a first adhesive layer;
    a second substrate sheet having on a front surface a plurality of second engaging elements engageable with said first engaging elements and on a rear surface a second adhesive layer; and
    wherein the first adhesive layer has an adhesive strength smaller than that of said second adhesive layer and smaller than an engaging strength of the first and second engaging elements when the first and second engaging elements are engaged with each other.

2. A surface fastener according to claim 1, wherein said first adhesive layer is an adhesive double coated tape having an outer surface, the outer surface of the tape having a backing sheet adhered thereto, and said second adhesive layer having an outer surface which has a peel paper adhered thereto.

3. A surface fastener according to claim 2, wherein said backing sheet has an outer surface having another adhesive layer thereon which adhesive layer has an outer surface to which another peel paper is adhered.

4. A surface fastener according to claim 1 or 2, wherein said second engaging elements of said second substrate sheet on which the second adhesive layer is disposed are loop-shaped engaging elements, and said first engaging elements of said first substrate sheet on which said first adhesive layer is disposed are hook-shaped engaging elements.

5. A surface fastener according to claim 1 or 2, wherein at least one of said first and second substrate sheets is knitted or woven, and said engaging elements of one of said first and second substrate sheets are hook-shaped engaging elements and/or loop-shaped engaging elements.

6. A surface fastener according to claim 4, wherein hook-shaped engaging elements are molded on said front surface of said first substrate sheet by injection molding.

7. A paper diaper comprising:
a unitary diaper body having a front covering portion having opposite free sides and a hip covering portion having opposite free sides, said hip covering portion having two attachment strips respectively disposed at said opposite sides, and two surface fasteners respectively releasably fastening said opposite free sides of said front covering portion to said opposite free sides of said hip covering portion, each of said fasteners comprising:
 a first substrate sheet having on a front surface a plurality of first engaging elements,
 a second substrate sheet having on a front surface a plurality of second engaging elements engageable with said first engaging elements and on a rear surface an adhesive layer adhered to one of said opposite free sides of said front covering portion, and
 an adhesive double coated tape adhered to a rear surface of said first substrate sheet with an adhesive strength smaller than that of said adhesive layer and smaller than an engaging strength of the first and second engaging elements when the first and second engaging elements are engaged with each other, said adhesive double coated tape being adhered to one of said attachment strips of said hip covering portion.

8. A paper diaper according to claim 7, further including a backing sheet adhered to an outer surface of said adhesive double coated tape, an additional adhesive layer on a surface of the backing sheet opposite to the tape, and an outer surface of said additional adhesive layer adhered to each of said attachment strips of said hip covering portion.

9. A paper diaper according to claim 7, wherein said second engaging elements of each said second substrate sheet on which the first-mentioned adhesive layer is disposed are loop-shaped engaging elements, and said first engaging elements of each said first substrate sheet on which said adhesive double coated tape is disposed are hook-shaped engaging elements.

10. A paper diaper according to claim 7, wherein at least one of said first and second substrate sheets is knitted or woven, and said engaging elements of one of said first and second substrate sheets are hook-shaped engaging elements and/or loop-shaped engaging elements.

11. A paper diaper according to claim 9, wherein said hook-shaped engaging elements are molded on said front surface of each said first substrate sheet by injection molding.

\* \* \* \* \*